United States Patent [19]

Dealy

[11] Patent Number: 4,464,928
[45] Date of Patent: Aug. 14, 1984

[54] METHOD OF MEASURING SHEAR STRESS

[76] Inventor: John M. Dealy, 305 Grosvenor Ave., Montreal, Canada, H3Z 2M1

[21] Appl. No.: 419,793

[22] Filed: Sep. 20, 1982

[51] Int. Cl.³ .......................................... G01N 11/00
[52] U.S. Cl. .......................................... 73/54; 73/60
[58] Field of Search ................................ 73/54, 60

[56] References Cited

FOREIGN PATENT DOCUMENTS 74639  6/1981  Japan ............................... 73/60

Primary Examiner—Gerald Goldberg
Assistant Examiner—Vincent P. Kovalick
Attorney, Agent, or Firm—Robert J. Schaap; Eric Fincham

[57] ABSTRACT

A method is disclosed for measuring the shear stress of a viscoelastic fluid wherein the force measured on a plate exerted by the fluid flowing coplanar therewith is measured.

9 Claims, 5 Drawing Figures

METHOD OF MEASURING SHEAR STRESS

The present invention relates to a method and apparatus for measuring wall shear stresses in viscous or viscoelastic liquids.

It is often desired to determine the viscoelastic properties of polymer solutions and melts. These properties are of interest to polymer chemists and physicists because of their relationship with molecular structure. In addition, the rheological properites of molten polymers are of vital importance in the plastics industry where they are used as a basis for comparing and evaluating various plastics materials as well as for quality control and the modelling of industrial melt processing operations such as the manufacture of plastic bottles and films.

Generally, there are two broad classes of rheological properties—first, those involving shearing at a steady rate and secondly, those involving shearing action that is a more complex function of time. These two types of deformation can generally be referred to as "steady shear" and "transient shear". Steady shear is useful to determine the viscosity of a fluid while transient shear tests are useful in determining the elastic properties of a fluid. Furthermore, one can categorize "small" and "large" transient tests. Small transient shearing tests such as small amplitude oscillatory shear provide information about viscoelasticity of the fluid in its "equilibrium" or unstrained state and are of interest to polymer chemists and physicists. They are of limited value, however, to those interested in commercial plastics processes, as these involve large transient deformations.

Although the prior art is replete with techniques for measuring rheological properties of molten polymers, only a few of these are suitable for the study of large transient deformations. The few instruments that have been developed for use with this important category of deformations are very complex and difficult to build and use. The principal barrier to the development of a simpler and more convenient technique is the unavailability of a method or device for measuring the local shear stress exerted by a flowing liquid on the surface of a wall bounding the flow.

According to the present invention, there is provided a method for measuring wall shear stresses in a liquid having a viscosity between about $10^6$ and about $10^{10}$ centipoise. This method comprises the steps of placing a movable plate in a hole or recessed area of the wall, said movable plate being coplanar with the wall and slightly smaller than the hole so that there is a small gap between the edge of the movable plate and the edge of the hole. The movable plate is free to move slightly in two directions, generally parallel to the wall. By measuring the force required to stop the motion of the plate, the equal and opposite force being exerted on the face of the plate by the liquid can be determined. This force, divided by the area of the plate, gives the shear stress in the liquid.

The method can be utilized both for taking rheological measurements, for example by means of its use in conjunction with a sliding plate or slit rheometer, as well as for continuous monitoring of industrial processes such as extrusion.

One can use a number of techniques to measure the force on the plate. For example, a piezoelectric crystal cut so that it is sensitive to shear stresses can be used. In another aspect of the invention, the plate can be mounted such that its motion in the direction of shear is resisted by an elastic element, so that the deflection of the plate in this direction is directly related to the force. For example the plate can be mounted on the end of a cantilever beam rigidly fixed at its opposite end. The deflection of the cantilever beam can be detected by strain gauges or by means of proximity-sensitive detectors based on capacitance or reflected light. Or the plate can be mounted on an assembly moving in a set of linear bearings, with the movement resisted by a spring. The movement of the plate mounting, and thus the deflection of the spring (extension or compression), can be monitored by means of a linear motion transducer, for example an LVDT. Finally, a small linear servomotor can be substituted for the spring in this latter arrangement with the motor providing a force exactly sufficient to maintain the deflection of the plate at zero. An advantage of this arrangement is that the net deflection of the plate is virtually zero so that the gap can be made extremely small to minimize its effect on the flow pattern in the liquid under study. Those skilled in the art would be able to devise other means of measuring the force on the plate.

The present method, as previously discussed, provides a simple inexpensive means of measuring the local wall shear stress in viscous or viscoelastic liquids, such as molten plastics and raw elastomers, having a viscosity between $10^6$ and $10^{10}$ centipoise.

Having thus generally described the invention, reference will be made to the accompanying drawings illustrating embodiments thereof, in which.

Figure 1:
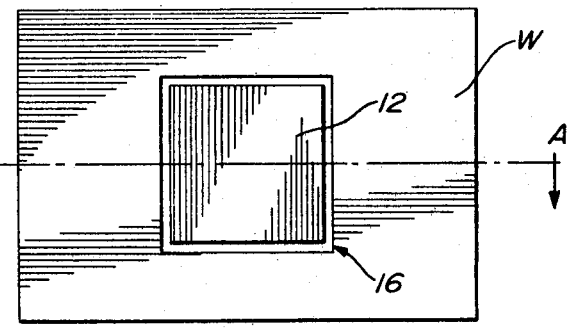
FIG. 1 is a view of the wall over which the liquid is flowing together with a cross-sectional view showing the movable plate used to measure the shear force.
Figure 1A:
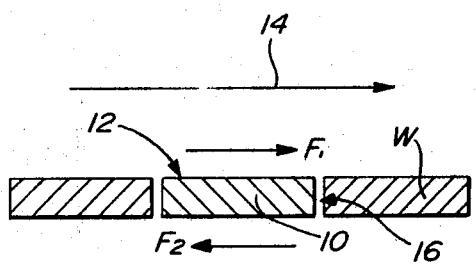
FIG. 1A is a cross-sectional view taken along the lines A—A of FIG. 1.

Referring to the drawings in greater detail and by reference characters thereto, the method of the present invention is illustrated in FIG. 1. As may be seen therein, a wall W has a plate segment designated by reference numeral 10 therein, which plate segment is movable and has a major face 12 thereof having an area A.

Liquid is caused to move over the face 12 as indicated by arrow 14, thereby causing a force as indicated by reference character $F_1$ on plate 10. The shear stress is accordingly equivalent to the reactive force $F_2$ divided by the area of face 12.

As will be readily appreciated, plate 10 is arranged such that the face 12 is of a planar nature and is substantially coplanar with wall W. The plate 10 must be mounted so that it is movable only in a direction parallel to the wall.

Plate 10 is slightly spaced from wall W leaving a minute gap 16 thereabout. Gap 16 might be in the order of between 0.1 mm and 1.0 mm. The width of the gap 16 should be minimized in order to minimize the amount of liquid that can enter the gap and affect the movement of plate 10. Naturally, with a viscous liquid the penetration through gap 16 would be extremely slow and initial readings would not be affected. Furthermore, if the shear stress is steady or changes slowly, the penetration poses only a minor problem as an equilibrium is achieved. However, if a transducer is to be used for transient shear measurements where the stress is changing rapidly, the liquid present is somewhat of a problem.

In order to overcome the above, one may fill gap 16 with an elastomeric material to prevent the flow of liquid therein. However, this does introduce a further factor into the measurement of the shear stress and this must be taken into account.

Figure 2:
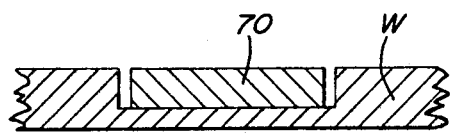
FIG. 2 is a cross-sectional schematic view of a possible arrangement using a piezoelectric crystal.

Turning to FIG. 2, in the embodiment illustrated, a piezoelectric quartz crystal 70 is mounted in wall structure W to be coplanar with the major face of the wall. The crystal 70 is a disc cut from a quartz crystal in such a way that when it is subjected to a shearing stress, an electrical charge appears at certain points. This charge can then be measured using conventional technology.

Figure 3:
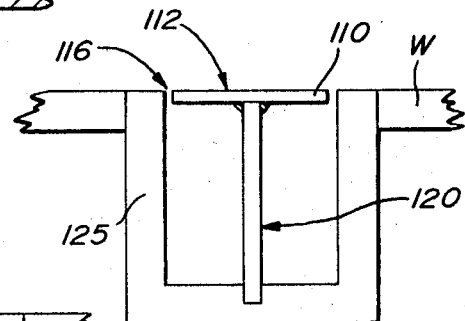
FIG. 3 is a cross-sectional view of an arrangement utilizing a cantilever beam.

In FIG. 3, a further embodiment is illustrated, in which plate 110 has a major face 112 and is separated from the surrounding wall structure by a gap 116. Beam 120 is mounted on the base of the casing 125 of the shear stress transducer. In order to measure the bending of the beam, and thus the shear stress, a variety of devices can be employed, including strain gauges, capacitance bridges and the intensity of light reflected from the beam into an optical fiber. This type of device is robust and simple to construct.

Figure 4:
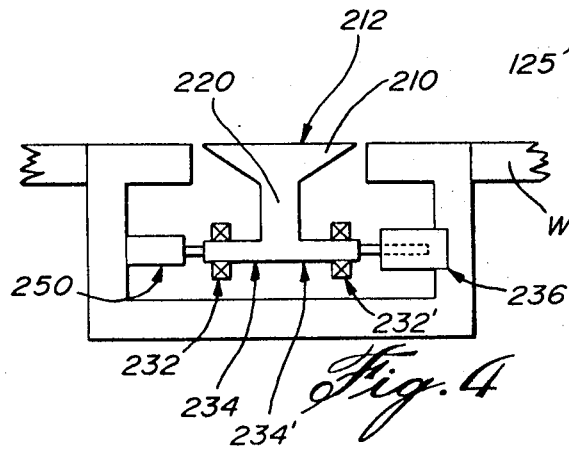
FIG. 4 is a cross-sectional schematic view of an arrangement involving the mounting of the plate on linear bearings together with the use of a linear displacement transducer.

Referring to FIG. 4, the arrangement shown therein employs a plate member 210 with face 212 mounted on an assembly 220 extending downwardly from plate 210. The assembly includes two pairs of rods 234, 234' supported by 4 linear bearings 232 and 232' respectively. A linear displacement transducer 236 (commercially available) may be employed to measure the movement of the assembly 220. The lateral movement of the assembly can be opposed by a spring 250 such that the displacement transducer 236 is directly related to the force exerted on the plate by the liquid.

If element 250 in FIG. 4 is taken to be a linear servomotor, then this arrangement represents a null meter in which the signal from the linear displacement motor is used as the error signal in a control loop that supplies just enough current to the servo motor to prevent the displacement of assembly 220. This current is thus directly related to the force being exerted on the assembly by the liquid. Utilizing such an embodiment, one minimizes the amount of the gap between the plate member and the wall. There must still exist a gap, but it is extremely small as no finite deflection occurs in operation. This method for measuring the force on the plate also minimizes the effect of the liquid in the gap on the frequency response.

It will be understood that the above-described embodiments are for purposes of illustration only and that changes and modifications may be made thereto without departing from the spirit and scope of the invention.

I claim:

1. A method of measuring the shear stress in a viscous or viscoeslastic liquid comprising in steps of:
   flowing said liquid past a plate member in a direction substantially parallel to a generally planar face thereof and measuring the force exerted on said plate in a direction substantially parallel to said face, said plate member being mounted such that the primary dynamic force acting thereon is said force parallel to said face.

2. The method of claim 1 wherein said plate is mounted in and coplanar with a wall and the step of measuring said force comprises the step of mounting the plate on a movable member and measuring the plate deflection in the direction of liquid flow.

3. The method of claim 1 wherein said plate is movable in the direction of fluid flow and the step of measuring the force comprises the step of measuring the force required to maintain said plate in its original position.

4. The method of claim 1, 2 or 3, wherein said liquid comprises a polymer solution, molten polymer or raw elastomer having a viscosity between about $10^6$ and about $10^{10}$ centipoise.

5. A method of measuring shear stresses in a liquid having a viscosity between about $10^6$ and about $10^{10}$ centipoise, the method comprising the steps of placing a movable plate in a wall, said movable plate being slightly spaced from a portion of a wall at its edges and being free to move in a direction parallel to the face thereof, flowing a liquid past the plate in a direction generally parallel to the face thereof and measuring the force exerted on said plate in a direction parallel to the face.

6. The method of claim 5 wherein said liquid comprises a polymer solution, molten polymer or raw elastomer.

7. The method of claim 5 wherein said movable plate is mounted on an elastic mounting and the force is measured by measuring the displacement of the plate in the direction of the stress.

8. The method of claim 5 wherein said force is measured by measuring the force necessary to prevent displacement of the plate in response to the shear stresses.

9. The method of claim 5 wherein said force is measured by applying an electrical field force to prevent displacement of the plate and measuring the strength of said electrical field force.

* * * * *